(12) United States Patent
Harwalkar

(10) Patent No.: US 12,299,891 B2
(45) Date of Patent: May 13, 2025

(54) METHOD AND SYSTEM FOR AUTOMATICALLY PROPAGATING SEGMENTATION IN A MEDICAL IMAGE

(71) Applicant: KONINKLIJKE PHILIPS N.V., Eindhoven (NL)

(72) Inventor: Pragati Harwalkar, Karnataka (IN)

(73) Assignee: KONINKLIJKE PHILIPS N.V., Eindhoven (NL)

(*) Notice: Subject to any disclaimer, the term of this patent is extended or adjusted under 35 U.S.C. 154(b) by 460 days.

(21) Appl. No.: 17/770,661

(22) PCT Filed: Oct. 30, 2020

(86) PCT No.: PCT/EP2020/080481
§ 371 (c)(1),
(2) Date: Apr. 21, 2022

(87) PCT Pub. No.: WO2021/084053
PCT Pub. Date: May 6, 2021

(65) Prior Publication Data
US 2022/0358659 A1  Nov. 10, 2022

(30) Foreign Application Priority Data
Oct. 31, 2019 (EP) .................................. 19206554

(51) Int. Cl.
*G06T 7/11* (2017.01)
*G06T 7/155* (2017.01)
(Continued)

(52) U.S. Cl.
CPC ................ *G06T 7/11* (2017.01); *G06T 7/155* (2017.01); *G06T 7/194* (2017.01); *G06T 7/62* (2017.01);
(Continued)

(58) Field of Classification Search
CPC . G06T 7/11; G06T 7/155; G06T 7/194; G06T 7/62; G06T 2207/20021;
(Continued)

(56) References Cited

U.S. PATENT DOCUMENTS 5,903,664 A  5/1999  Hartley
8,064,673 B2  11/2011  Kirchberg
(Continued)

FOREIGN PATENT DOCUMENTS

| WO | WO2013001471 A2 | 1/2013 |
| WO | WO2015008178 A1 | 1/2015 |
| WO | WO2018222755 A1 | 12/2018 |

OTHER PUBLICATIONS

PCT International Search Report, International application No. PCT/EP2020/080481, Feb. 10, 2021.
(Continued)

*Primary Examiner* — Md K Talukder

(57) ABSTRACT

Disclosed herein is a method and system for automatically propagating segmentation in a medical image. In an embodiment, the method uses a segmented reference Region of Interest (RoI) in a reference image to determine segmentation parameters and a plurality of reference points. Further, method generates a plurality of translated points on a current image, in which a target RoI must be segmented, by translating the plurality of reference points onto the current image. Subsequently, relevant seeds among from the translated points are automatically selected based on the segmentation parameters. Finally, a multi-seed segmentation of the selected relevant seeds is performed for estimating and segmenting the target RoI in the current image, such that the target RoI is the propagated segmentation of the segmented RoI in the reference image.

19 Claims, 8 Drawing Sheets

(51) Int. Cl.
  *G06T 7/194* (2017.01)
  *G06T 7/62* (2017.01)
  *G16H 30/40* (2018.01)

(52) U.S. Cl.
  CPC ... *G16H 30/40* (2018.01); *G06T 2207/20021* (2013.01); *G06T 2207/20036* (2013.01); *G06T 2207/30004* (2013.01)

(58) Field of Classification Search
  CPC . G06T 2207/20036; G06T 2207/30004; G06T 2207/20156; G06T 7/187; G06T 7/174; G06T 5/40; G06T 7/136; G06T 2207/20104; G16H 30/40
  See application file for complete search history.

(56) References Cited

U.S. PATENT DOCUMENTS

| | | |
|---|---|---|
| 9,773,325 B2 | 9/2017 | Plakas |
| 10,102,626 B2 | 10/2018 | Chou |
| 2008/0260221 A1* | 10/2008 | Unal ................ G06T 7/149 382/128 |
| 2014/0341452 A1 | 11/2014 | Kaftan |
| 2017/0039725 A1* | 2/2017 | Dror ................. G06T 7/12 |
| 2020/0151860 A1* | 5/2020 | Safdarnejad ........... G06T 7/162 |
| 2022/0358659 A1* | 11/2022 | Harwalkar ............. G06T 7/62 |
| 2022/0370033 A1* | 11/2022 | Klingensmith ........ A61B 34/10 |

OTHER PUBLICATIONS

Fanman M. et al., "Seeds-Based Part Segmentation by Seeds Propagation and Region Convexity Decomposition", IEEE Transactions on Multimedia., vol. 20, No. 2, Feb. 1, 2018 (Feb. 1, 2018), pp. 310-322, XP055688719.

Smistad E. et al., "Medical Image Segmentation on GPUs—A Comprehensive Review", Medical Image Analysis, vol. 20, No. 1, Feb. 1, 2015 (Feb. 1, 2015), pp. 1-18, XP055689149.

* cited by examiner

Reference points 213        Translated points 215

Translated points 215       Relevant seeds 311

Relevant seeds 311  Region obtained using relevant seeds 311

Overlapping region 313  Target RoI 109

METHOD AND SYSTEM FOR AUTOMATICALLY PROPAGATING SEGMENTATION IN A MEDICAL IMAGE

FIELD OF THE INVENTION

The present subject matter is, in general, related to the field of image processing techniques, and more particularly, but not exclusively, to a method and system for automatically propagating segmentation in a medical image.

BACKGROUND OF THE INVENTION

Medical imaging has emerged as a primary tool for diagnosis of several diseases. Medical imaging is the process of creating visual representations of an interior of a body for clinical analysis and medical intervention, as well as for functional analysis of internal organs or tissues in the body. Generally, the visual representations may be in the form of images and videos. One of the first and most important process used for analyzing the visual representations is segmentation. Segmentation is the process of partitioning an image into different meaningful segments, which correspond to different tissue classes, organs, pathologies, or other biologically relevant structures.

In general, the human anatomy consists of many types of tissues. Consequently, in certain diagnostic processes, particularly in the diagnosis of tumors, a single tissue may appear differently in different modalities. Hence, using a common segmentation process, such as a computer-based automatic tumor segmentation has remained an ongoing challenge in the diagnosis of tumors.

Also, most of the existing segmentation procedures are tailored for segmenting tumors in the images of specific modalities and for a particular anatomy. Thus, presently, there still is need for segmentation techniques that are generic across modalities and anatomies.

The information disclosed in this background of the disclosure section is only for enhancement of understanding of the general background of the invention and should not be taken as an acknowledgement or any form of suggestion that this information forms the prior art already known to a person skilled in the art.

SUMMARY OF THE INVENTION

Disclosed herein is a method for automatically propagating segmentation in a medical image. The method comprises determining one or more segmentation parameters based on analysis of a segmented reference Region of Interest (RoI) in a reference image. Further, the method comprises determining a plurality of reference points corresponding to the segmented reference RoI based on one or more morphological characteristics of the segmented reference RoI. Upon determining the plurality of reference points, the method comprises generating a plurality of translated points on a current image, in which a target RoI has to be segmented, by translating each of the plurality of reference points onto the current image. Furthermore, the method comprises automatically selecting relevant seeds in the current image, from the plurality of translated points, based on the one or more segmentation parameters. Finally, the method comprises performing a multi-seed segmentation of the selected relevant seeds for estimating and segmenting the target RoI in the current image, wherein the target RoI is the propagated segmentation of the segmented RoI in the reference image and wherein pixel intensities of the current image are quantitatively comparable or can be normalized to pixel intensities of the reference image.

Further, the present disclosure relates to an image segmentation system for automatically propagating segmentation in a medical image. The image segmentation system comprises a processor and a memory, communicatively coupled to the processor. The memory stores processor-executable instructions, which on execution causes the processor to determine one or more segmentation parameters based on analysis of a segmented reference Region of Interest (RoI) in a reference image. Further, the instructions cause the processor to determine a plurality of reference points corresponding to the segmented reference RoI based on one or more morphological characteristics of the segmented reference RoI. Thereafter, the instructions cause the processor to generate a plurality of translated points on a current image, in which a target RoI has to be segmented, by translating each of the plurality of reference points onto the current image. Furthermore, the instructions cause the processor to automatically select relevant seeds in the current image, from the plurality of translated points, based on the one or more segmentation parameters. Finally, the instructions cause the processor to perform a multi-seed segmentation of the selected relevant seeds to estimate and segment the target RoI in the current image, wherein the target RoI is the propagated segmentation of the segmented RoI in the reference image and wherein pixel intensities of the current image are quantitatively comparable or can be normalized to pixel intensities of the reference image.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The accompanying drawings, which are incorporated in and constitute a part of this disclosure, illustrate exemplary embodiments and, together with the description, explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and regarding the accompanying figures, in which.

Figure 1:
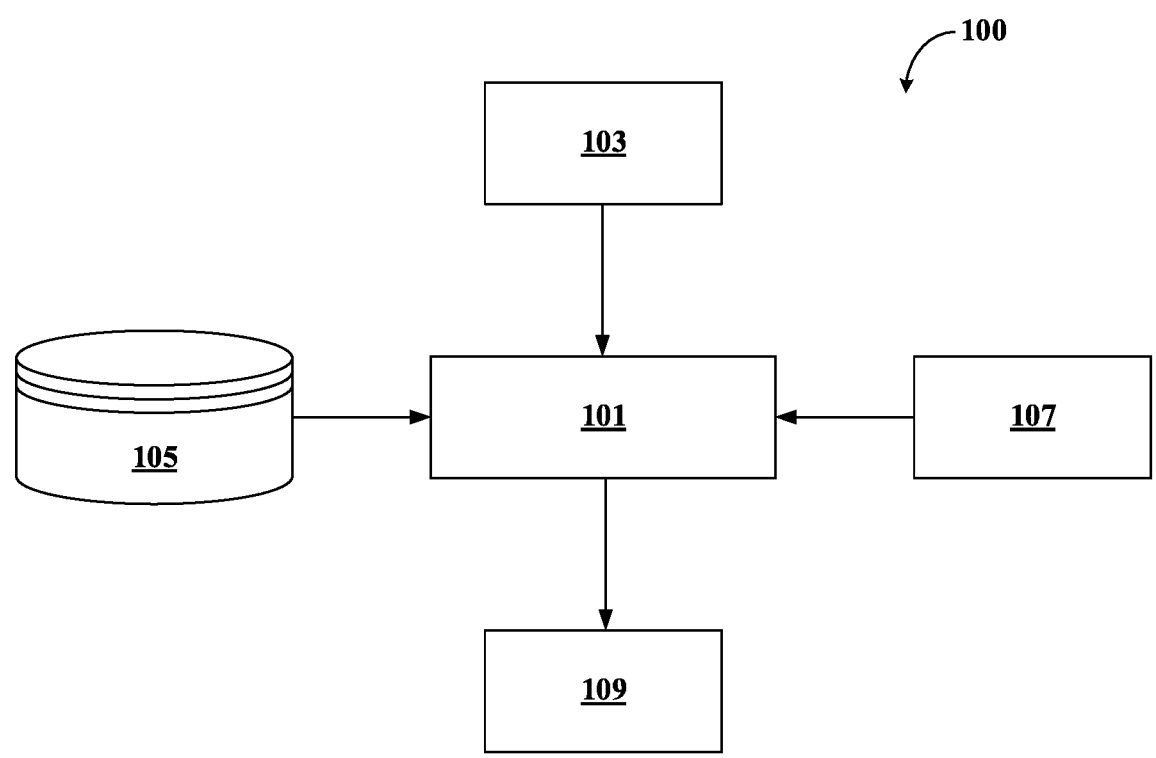
FIG. 1 illustrates an exemplary environment for automatically propagating segmentation in medical images in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether such computer or processor is explicitly shown.

DETAILED DESCRIPTION OF EMBODIMENTS

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the specific forms disclosed, but on the contrary, the disclosure is to cover all modifications, equivalents, and alternative falling within the spirit and the scope of the disclosure.

The terms "comprises", "comprising", "includes", or any other variations thereof, are intended to cover a non-exclusive inclusion, such that a setup, device, or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

Embodiments of the present disclosure may be used for automatically propagating segmentation of lesions through one or more follow-up sessions for oncology during periodic scans of the lesions and/or other affected regions.

Accordingly, in an embodiment, the present disclosure discloses a method and an image segmentation system for automatically propagating segmentation in a medical image. In an embodiment, the method of present disclosure comprises picking up reference points corresponding to a segmented Region of Interest (RoI) of reference image and/or reference study and translating the reference points to a current image of the lesion captured in the follow-up session to perform multi-seed segmentation. Multi-seed segmentation of the selected relevant reference points on the current image helps in estimating and segmenting a target RoI in the current image. In an embodiment, the target RoI may be a propagated segmentation of the segmented RoI in the reference image. Thus, the present disclosure helps in automatically propagating the segmentation in medical images.

In an embodiment, the present disclosure performs segmentation of lesion for any anatomical region and for any modality to infer required parameters from the segmented lesion. As an example, the parameters that may be inferred may include, without limiting to, size, shape, position, intensity distribution of the lesion, homogeneity/heterogeneity of lesion and appearance of surrounding background tissue of the lesion.

In an embodiment, the present disclosure addresses a technical problem of repetitive segmentation of lesion in the follow-up scans by automating the propagation of segmentation using the information of lesion segmented in the first scan.

In an embodiment, the method and the image segmentation system disclosed in the present disclosure may be used for propagation of the segmentation of objects/entities having similar features in more than one studies such as scans, images, volumes, when segmentation of the object/entity is available in at least one of such studies.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

FIG. 1 illustrates an exemplary environment for automatically propagating segmentation in medical images in accordance with some embodiments of the present disclosure.

The environment 100 may include an image segmentation system 101 and a reference database 105 associated with the image segmentation system 101. In an embodiment, the image segmentation system 101 may be a computing device such as, without limiting to, a desktop computer, a laptop, a smartphone or a server, which may be configured for automatically propagating segmentations in medical images in accordance with the embodiments of the present disclosure. In an embodiment, the reference database 105 may be a storage unit used for storing information related to patients, historical medical images and/or historical reference image 103 related to the patients and other information required for propagating the segmentation. In an implementation, the reference database 105 may be a part of the image segmentation system 101 and present within the image segmentation system 101.

In an embodiment, the reference image 103 and the current image 107 may be images of entities such as organs, tissues, bones, air cavities and muscles of a subject, which are captured at different time periods. Here, the subject may be a human being, an animal and the like. Further, as an example, the reference image 103 may be an image of an entity captured during an initial study of the entity, from which a reference Region of Interest (RoI) may be segmented. The current image 107 may be an image of the same entity captured during a subsequent study of the subject. In an embodiment, the reference image 103 and the current image 107 may be captured by an external equipment such as a Computed Tomography (CT) scanner, a Magnetic Resonance Imaging (MM) device and the like. In an embodiment, the image segmentation system 101 may receive the reference image 103 and the current image 107 from one of the medical equipment or a reference database using a wired and/or a wireless communication interface configured between the image segmentation system 101 and the external equipment. In an implementation, the image segmentation system 101 and the external equipment may be implemented as a single system, which performs both scanning and segmentation.

In an embodiment, upon capturing the reference image 103 of the entity, a technical expert associated with the image segmentation system 101 may manually perform segmentation of the reference image 103 to mark and/or to obtain the reference RoI from the reference image 103.

Subsequently, upon capturing the current image 107 of the entity, the current image 107, along with the reference image 103 and the segmented reference RoI, may be provided as an input to the image segmentation system 101 for automatically performing segmentation of the current image 107.

In an embodiment, upon receiving the reference image 103, the current image 107 and the reference RoI, the image segmentation system 101 may determine one or more segmentation parameters related to the reference image 103 based on analysis of the segmented reference RoI in the reference image 103. In an embodiment, the one or more segmentation parameters determined from the reference image 103 may include, without limiting to, one or more morphological characteristics of the segmented reference RoI, a position of the segmented reference RoI within the reference image 103, an intensity distribution of the segmented reference RoI, and a background intensity distribution of a background of the segmented reference RoI.

In an embodiment, the one or more morphological characteristics may include, without limiting to, a short axis and a longest diameter of the segmented reference RoI and size and shape of the segmented reference RoI. In an embodiment, the size and shape of the segmented reference RoI may be determined based on length and coordinates of the short axis and the longest diameter of the segmented reference RoI.

In an embodiment, the intensity distribution of the segmented reference RoI may be variation of pixel intensities in the region of the segmented reference RoI. Similarly, the background intensity distribution of the background of the segmented reference RoI may be the variation of pixel intensities in the region around the segmented reference RoI. In an embodiment, the intensity distribution of the background of segmented reference RoI may be determined by determining a plurality of intensity distributions of a plurality of background pixels/points corresponding to quadrants of the segmented reference RoI, with respect to a centre of the segmented reference RoI. In an embodiment, the intensity distribution ranges may be determined based on an amount of overlapping between the pixel intensities of the respective background of the plurality of background quadrants and pixel intensities of the segmented reference RoI.

In an embodiment, upon determining the one or more segmentation parameters from the segmented reference RoI, the image segmentation system 101 may determine a plurality of reference points corresponding to the segmented reference RoI based on the one or more morphological characteristics of the segmented reference RoI. In an embodiment, the plurality of reference points may be the points located along the short axis and the longest diameter of the segmented reference RoI.

In an embodiment, subsequent to determining the plurality of reference points, the image segmentation system 101 may generate a plurality of translated points on the current image 107 of the entity, in which a target RoI 109 has to be segmented. In an embodiment, the plurality of translated points may be obtained by translating each of the plurality of reference points onto the current image 107.

In an embodiment, upon generating the plurality of translated points, the image segmentation system 101 may automatically select relevant seeds among the plurality of translated points in the current image 107, based on the one or more segmentation parameters.

In an embodiment, once the relevant seeds are selected from the plurality of translated points, the image segmentation system 101 may perform a multi-seed segmentation of the selected relevant seeds for estimating and segmenting the target RoI 109 in the current image 107. In an embodiment, the target RoI 109 may correspond to a propagated segmentation of the segmented RoI in the reference image 103. In an embodiment, a prerequisite condition for performing the segmentation of the target RoI 109 may be that the pixel intensities of the current image 107 must be quantitatively comparable or normalized to the pixel intensities of the reference image 103.

In an embodiment, after segmenting the target RoI 109 from the current image 107, the target RoI 109 may be compared against the segmented reference RoI to determine changes in the respective one or more segmentation parameters of the segmented reference RoI and the target RoI 109. In an embodiment, during subsequent studies of the entity, the current image 107 of the entity and the segmented target RoI 109 together may be considered as the reference image 103 having the reference segmented RoI.

Figure 2:
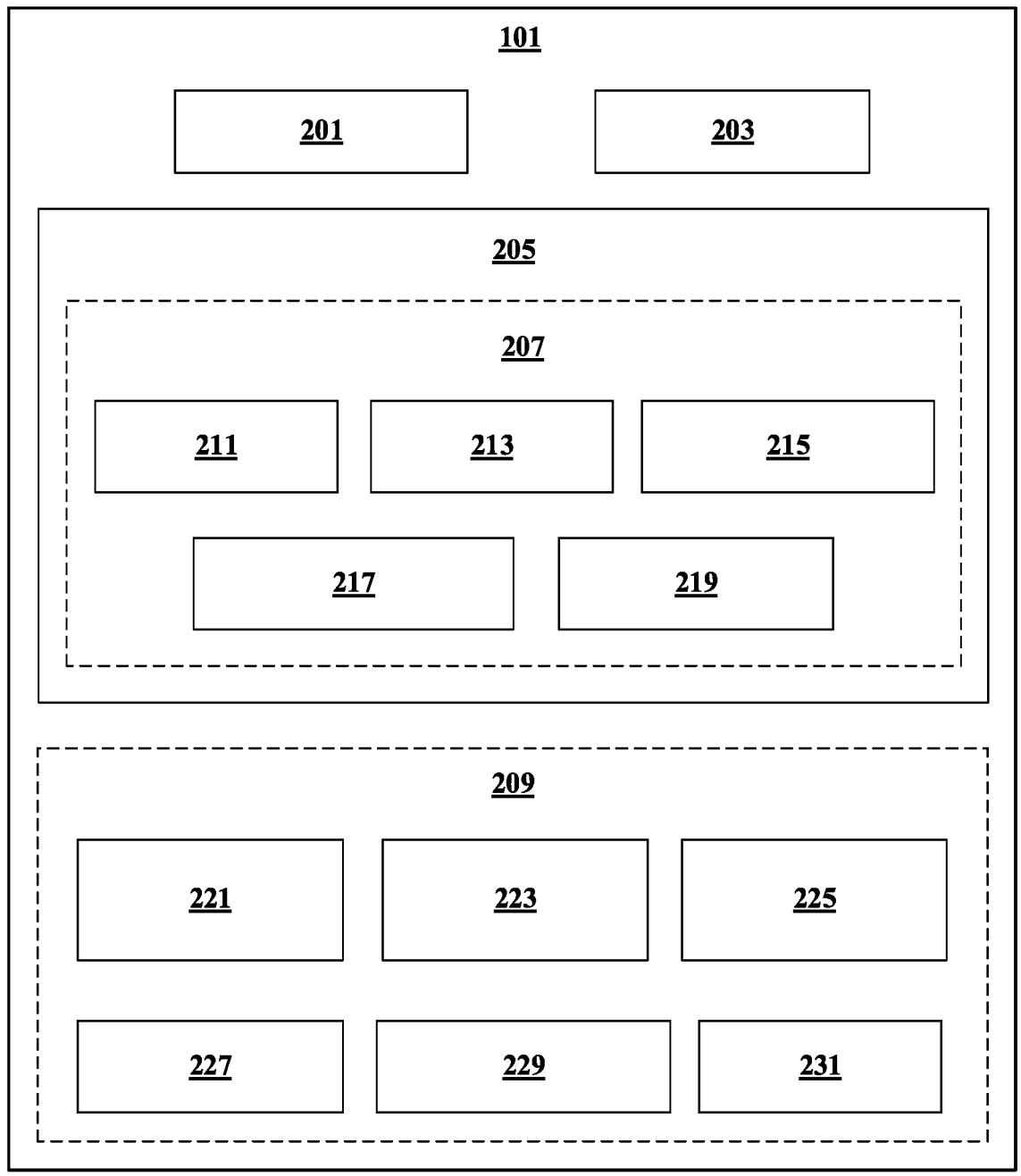
FIG. 2 shows a detailed block diagram illustrating an image segmentation system for automatically propagating the segmentation in accordance with some embodiments of the present disclosure.

FIG. 2 shows a detailed block diagram illustrating an image segmentation system 101 for automatically propagating the segmentation in accordance with some embodiments of the present disclosure.

In an implementation, the image segmentation system 101 may include an I/O interface 201, a processor 203, and a memory 205. The I/O interface 201 may be configured to communicate with one or more sources and/or external equipment for receiving a reference image 103 and a current image 107. Further, the I/O interface 201 may be used to connect the image segmentation system 101 to a display interface for displaying the reference image 103, the current image 107 and segmented regions of the images to a user. In an embodiment, the memory 205 may be communicatively coupled to the processor 203. The processor 203 may be configured to perform one or more functions of the image segmentation system 101.

In some implementations, the image segmentation system 101 may include data 207 and modules 209 for performing various operations in accordance with the embodiments of the present disclosure. In an embodiment, the data 207 may be stored within the memory 205 and may include, without limiting to, one or more segmentation parameters 211, a plurality of reference points 213, a plurality of translated points 215, a Target Region of Interest (RoI) 217 and other data 219.

In some embodiments, the data 207 may be stored within the memory 205 in the form of various data structures. Additionally, the data 207 may be organized using data models, such as relational or hierarchical data models. The other data 219 may store temporary data and temporary files, generated by the modules 209 while performing various functions of the image segmentation system 101. As an example, the other data 219 may include, without limiting to, one or more historical or reference image 103 of the entity, morphological characteristics of the segmented RoIs and the like.

In an embodiment, the data 207 may be processed by one or more modules 209 of the image segmentation system 101. As used herein, the term module refers to an Application Specific Integrated Circuit (ASIC), an electronic circuit, a processor (shared, dedicated, or group) and memory that execute one or more software or firmware programs, a combinational logic circuit, and/or other suitable components that provide the described functionality. In an embodiment, the other modules 231 may be used to perform various miscellaneous functionalities of the image segmentation system 101. It will be appreciated that such modules 209 may be represented as a single module or a combination of different modules.

In one implementation, the one or more modules 209 may be stored as instructions executable by the processor 203. In another implementation, each of the one or more modules 209 may be separate hardware units, communicatively coupled to the processor 203 for performing one or more functions of the image segmentation system 101. The one or more modules 209 may include, without limiting to, a parameter determination module 221, a reference point determination module 223, a seed generation module 225, a seed selection module 227, a segmentation module 229 and other modules 231.

In an embodiment, the parameter determination module 221 may be used for determining one or more segmentation parameters 211 based on analysis of the segmented reference RoI in the reference image 103. In an embodiment, the foremost step towards propagating segmentation of the reference image 103 may be determination of the one or more segmentation parameters 211 such as, without limiting to, one or more morphological characteristics of the segmented reference RoI, a position of the segmented reference RoI within the reference image 103, an intensity distribution of the segmented reference RoI, and an intensity distribution of a background of the segmented reference RoI.

In an embodiment, the parameter determination module 221 may determine the one or more morphological characteristics of the segmented reference RoI by determining a short axis and a longest diameter of the segmented reference RoI and then determining a size and a shape of the segmented reference RoI based on length and coordinates of the short axis and the longest diameter of the segmented reference RoI. Further, the position of the segmented reference RoI within the reference image 103 may be determined based on co-ordinates of the points on the short axis and the longest diameter.

In an embodiment, the parameter determination module 221 may determine the intensity distribution of the segmented reference RoI by computing a histogram of intensity of the pixels forming the segmented reference RoI. In addition, the parameter determination module 221 may derive a heterogeneity of the segmented reference RoI by thresholding the histogram at a predetermined frequency. For example, the pixel intensity values having frequency values greater than 60% of the highest frequency value in the histogram may be considered. The thresholding may result in a number of pixel intensity ranges, referred as Lesion Range (Lr). In an embodiment, if the segmented reference RoI is homogeneous, then there may be only a single pixel intensity range. On the other hand, if the segmented reference RoI is heterogeneous, then thresholding of the histogram may result in multiple pixel intensity ranges.

In an embodiment, the parameter determination module 221 may determine the intensity distribution of the background and/or surrounding region of the segmented reference RoI by a process that is similar to computation of the histogram. That is, the intensity distribution may be determined by computing the histogram and then thresholding the histogram with the predetermined frequency. However, this may be done by grouping the pixels into four quadrants based on their co-ordinates, with centre of the segmented reference RoI as the origin for the quadrants. Consequently, there may be four histograms corresponding to each of the four quadrants and four groups of pixel intensity ranges resulting from thresholding of the histograms. These pixel intensity ranges may be referred as Background range (BGr).

In an embodiment, subsequent to obtaining the Lr and four BGr, the parameter determination module 221 may compute a Neighbor Threshold (NT) and a Background Histogram percent (BbHp). In an embodiment, the NT may represent a minimum number of neighboring pixels of a point that must satisfy the Lr and BGr criteria for that point to be shortlisted and/or selected as the reference point. In an embodiment, the BgHp may represent an actual background histogram threshold percentage that may be considered for intensity comparison for shortlisting a relevant reference seed.

In an embodiment, the parameter determination module 221 may determine the background parameters using the following method. Initially, for each quadrant, the background histogram may be thresholded with multiple frequency ranges like 10%, 30%, 50% and 70%. Thus, at the end of thresholding, the BGr may be obtained for every frequency threshold for each quadrant of the background pixels. In an embodiment, an overlap between the Lr and each of the BGr may be computed and the values of NT and BgHp may be derived iteratively as illustrated in Table A and Table B below.

In an embodiment, the criteria for deriving parameters may be different for different types and/or sources of the images. For example, the criteria for deriving parameters of images obtained from Computer Tomography (CT) may be as shown in Table A. Similarly, the criteria for deriving parameters of images obtained from Magnetic Resonance Imaging (MRI) may be as shown in Table B.

TABLE A

Deriving parameters for CT scans

| | | Overlap percentage | | | | |
|---|---|---|---|---|---|---|
| | | 0% (No overlap) | >99% (Full overlap) | >0%-30% | 30%-60% | 60%-99% |
| Background Histogram Frequency Percentage | 70% | NT = 3<br>BgHp = 50 | NT = 3<br>BgHp = 70 | NT = 2<br>BgHp = 50 | NT = 2<br>BgHp = 70 | NT = 1<br>BgHp = 70 |
| | 50% | NT = 3<br>BgHp = 30 | NT = 3<br>BgHp = 50 | NA | NA | NA |
| | 30% | NT = 3<br>BgHp = 10 | NT = 3<br>BgHp = 30 | NA | NA | NA |

TABLE B

| Deriving parameters for MRI scans | | | | | |
|---|---|---|---|---|---|
| | | Overlap count | | | |
| | | | >2 Overlap percentage | | |
| | <=2 | >99% (Full overlap) | >0%-30% | 30%-60% | 60%-99% |
| Background Histogram Frequency Percentage | 70% NT = 3 BgHp = 50 | BgHp = 70 NT = 3 | NT = 3 | NT = 2 | NT = 1 |
| | 50% NT = 3 BgHp = 30 | BgHp = 50 NT = 2 | | | |
| | 30% NT = 3 BgHp = 10 | BgHp = 30 NT = 2 | | | |

In an embodiment, the overlap percentage (shown in Table A and Table B) may be the percentage of Lr that is overlapping with BGr. Further, the overlap count (shown in Table B) may be the number of quadrants of BGr that has overlap with Lr.

In an embodiment, the reference point determination module 223 may be used for determining the plurality of reference points 213 corresponding to the segmented reference RoI based on the one or more morphological characteristics of the segmented reference RoI. In an embodiment, since the longest diameter and the short axis of the segmented reference RoI, determined based on the reference study of the reference image 103, lie on cross section of the RoI, the longest diameter and the short axis may be considered to cover most of the distinct intensity regions in the segmented RoI. Therefore, in an embodiment, the plurality of reference points 213 on the segmented reference RoI may be determined as co-ordinates of discrete points identified on the longest diameter and the short axis.

Figure 3A:
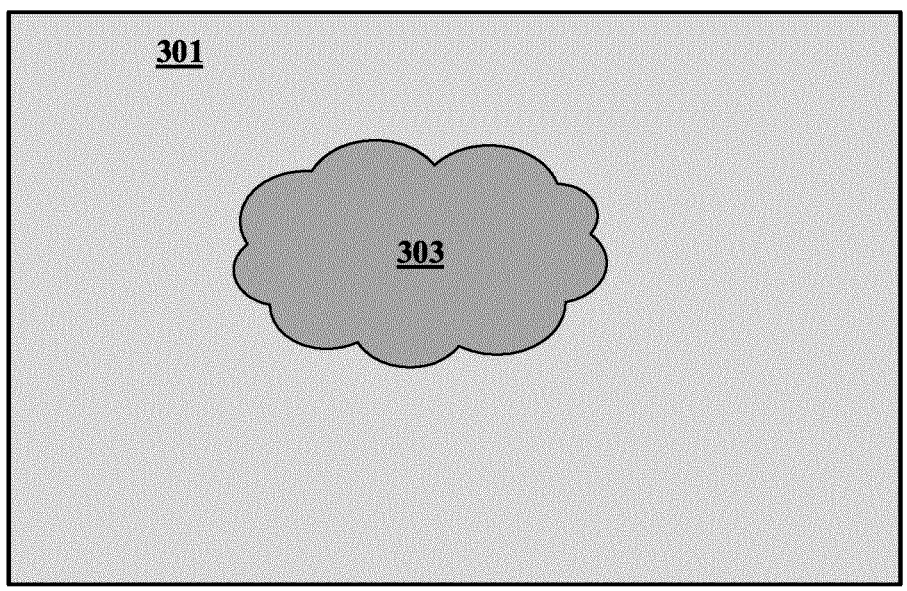
FIG. 3A-3H illustrate the process of propagating segmentation with respect to a reference image and a current image in accordance with an exemplary embodiment of the present disclosure.
Figure 3B:
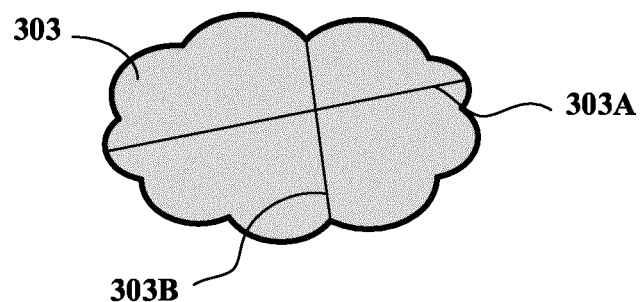
Figure 3C:
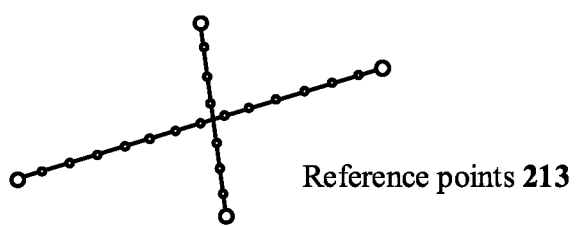

In an embodiment, the process of obtaining the reference RoI and determining the plurality of reference points 213 on the reference RoI may be illustrated using exemplary representations in FIG. 3A-FIG. 3C.

FIG. 3A shows a reference image 103 comprising a reference RoI 303. FIG. 3B indicates a longest diameter 303A and a short axis 303B for the segmented reference RoI 303. Now, the plurality of reference points 213 corresponding to the segmented reference RoI 303 may be determined by identifying a discrete set of points on the longest diameter 303A and the short axis 303B of the segmented reference RoI 303, as shown in FIG. 3C.

Figure 3D:
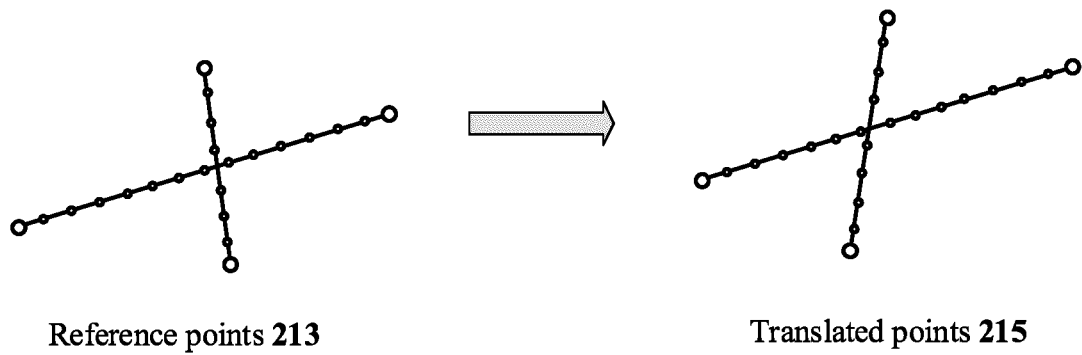

In an embodiment, the seed generation module 225 may be used for generating a plurality of translated points 215 on the current image 107, in which the Target RoI 109 has to be segmented, by translating each of the plurality of reference points 213 onto the current image 107. In an embodiment, once all the reference points 213 have been determined and extracted from the reference image 103, the seed generation module 225 may transform each of the plurality of reference points 213 to the current image 107 to get the plurality of translated points 215 on the current image 107. That is, the reference points 213 determined from the reference image 103 may be transformed into the current image 107 as translated points 215, as shown in FIG. 3D.

Figure 3E:
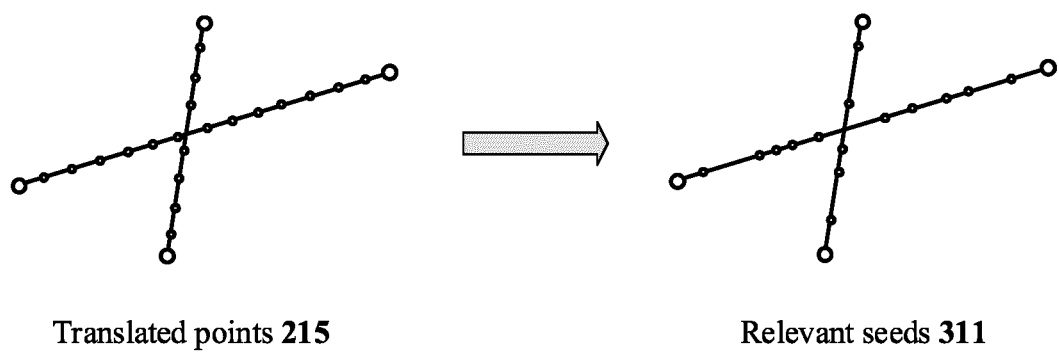

In an embodiment, the seed selection module 227 may be used for automatically selecting relevant seeds 311 in the current image 107, from the plurality of translated points 215, based on the one or more segmentation parameters 211. FIG. 3E shows the relevant seeds 311 that are shortlisted and selected from the translated points 215. In an embodiment, the pixel intensity ranges corresponding to the segmented reference RoI 303 and for each of the four quadrants of the background pixels may be the most critical segmentation parameters 211 used for selecting the relevant seeds 311 in the current image 107.

In an embodiment, one of the plurality of translated points 215 'P', may be shortlisted as the relevant seed, only if the seed point 'P' satisfies one or more conditions defined below:

1. The pixel intensity of point P is within the range as defined by Lr.
2. The pixel intensity of point P is outside the background intensity range BGr. Here, the background intensity range may be the set of intensity ranges obtained by thresholding the histogram by BgHp of the background pixels of a quadrant to which the point P belongs.
3. Number of immediate neighbors of point P that satisfy the above conditions 1 and 2 is greater than or equal to NT.
4. The intensity Ip of the point P is such that:

Ip<Lr<BGr or

Ip>Lr>BGr

In an embodiment, the Point P may be shortlisted when the point P satisfies all the three conditions 1, 2 and 3 above or when the point P satisfies only the condition 4 above.

In an embodiment, if the point P is not shortlisted, then a neighbor point of the point P may be checked and shortlisted if the neighbor point satisfies the conditions 1, 2 and 3 above.

In an embodiment, after repeating the above analysis for all the points of the plurality of translated points 215, if none of the plurality of translated points 215 get shortlisted, then the translated points 215 that satisfy only condition 1 may be shortlisted as the relevant seeds 311.

In an embodiment, in case of CT images, the bilateral filtered pixel intensity of point P may be used against all the conditions 1-4 mentioned above. Whereas, for MR images no filtering may be applied and the pixel intensity may be directly compared. Also, in the CT images, the intensities represent a quantitative information and hence two CT scans may be compared directly. However, in MR images, since the intensities of the pixels only represent a qualitative information, the two scans, which are of same variants, may have to be normalized first before comparing.

In an embodiment, the segmentation module 229 may be used for performing a multi-seed segmentation of the selected relevant seeds 311 for estimating and segmenting a target RoI 109 in the current image 107. In an embodiment, the multi-seed segmentation may be considered as an extension of single seed segmentation technique, which is implemented to address heterogeneity of the reference RoI, for all the selected relevant seed points obtained in the above process. In an embodiment, multi-seed segmentation of the selected relevant seeds 311 may be performed using one of the existing multi-seed segmentation techniques such as parametric method, level-set method, clustering method and the like. Alternatively, the multi-segmentation may also be performed using a region-growing technique, as illustrated in the present disclosure.

In an embodiment, the segmentation module 229 may receive a user input, indicating whether the target RoI 109 determined in the current image 107 is bigger than, or smaller than or of same size as that of the reference RoI determined in the reference image 103. This user input may be used to limit the area to be searched and/or scanned while performing the multi-seed segmentation.

In an embodiment, if the target RoI 109 in the current image 107 is bigger than that of the reference RoI, then the search area radius may be set equal to the longest diameter of the reference RoI.

In an embodiment, if the target RoI 109 is smaller than that of the reference RoI, then the search area radius may be set to 50% of the longest diameter of the reference lesion.

In an embodiment, if the target RoI 109 is of the same size of the reference RoI, then search area radius may be set to 75% of the longest diameter of the reference lesion.

That is, the difference in the size of the target RoI 109 and the size of the reference RoI may be correlated and adjusted using one of the above adjustments.

Figure 3F:
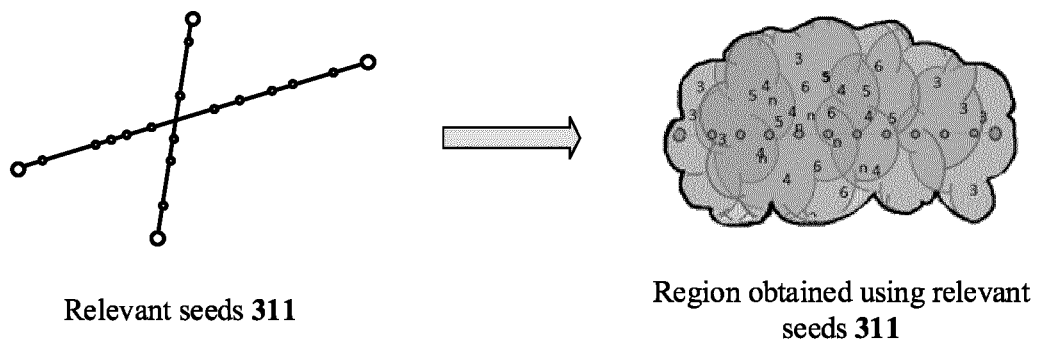

FIG. 3F indicates the region obtained by performing the multi-seed segmentation of the relevant seeds 311 on the current image 107. In an embodiment, the multi-seed segmentation may exclude some areas of the target RoI 109, having dissimilar intensities in comparison to the overall intensity of the RoI, from generating the target RoI 109. However, this may be addressed by using an intensity-based k-means clustering region growing technique in the region defined by the multi-seed segmentation output.

Figure 3G:
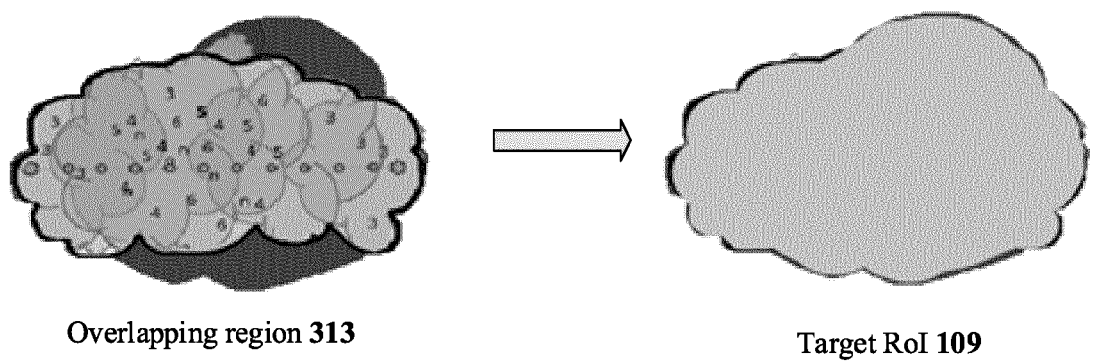
Figure 3H:
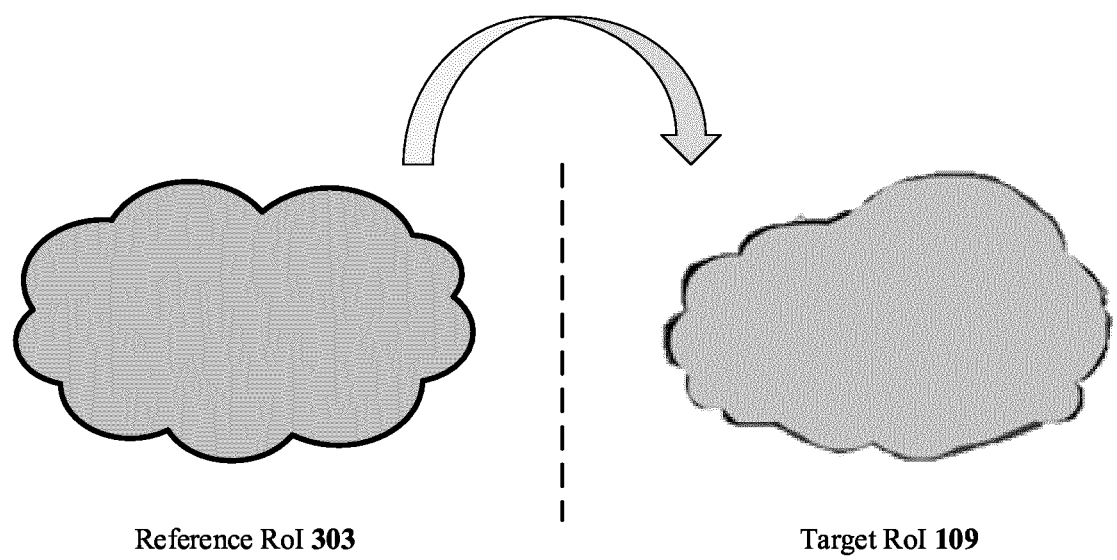

In an embodiment, the region obtained by performing the multi-seed segmentation of the relevant seeds 311 may be used to determine an overlapping region 313 on the current image 107. Thereafter, the overlapping region 313 may be extracted from the current image 107 and treated as the target RoI 109 corresponding to the current image 107, as show in FIG. 3G. That is, FIG. 3G indicates the target RoI 109 extracted by performing the above steps on the current image 107.

In an embodiment, a comparison of the reference RoI and the target RoI 109, as shown in FIG. 311, helps in determining changes in the RoI across the reference image 103 and the current image 107 of the same entity.

Figure 4:
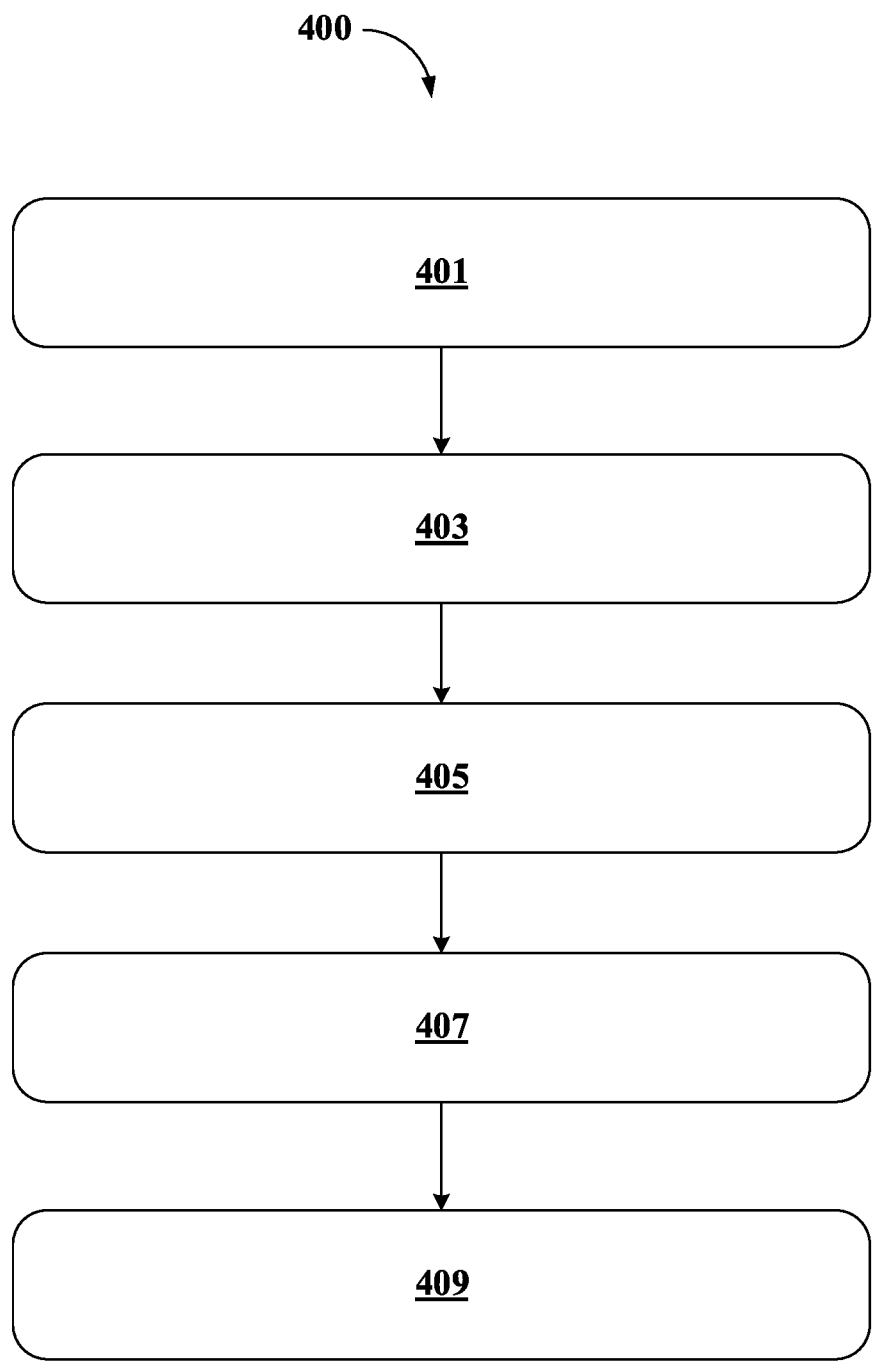
FIG. 4 shows a flowchart illustrating a method for automatically propagating segmentation in medical images in accordance with some embodiments of the present disclosure.

FIG. 4 shows a flowchart illustrating a method for automatically propagating segmentation medical images in accordance with some embodiments of the present disclosure As illustrated in FIG. 4, the method 400 includes one or more blocks illustrating a method for automatically propagating segmentation in medical images using an image segmentation system 101, illustrated in FIG. 1. The method 400 may be described in the general context of computer executable instructions. Generally, computer executable instructions can include routines, programs, objects, components, data structures, procedures, modules, and functions, which perform specific functions or implement specific abstract data types.

The order in which the method 400 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At block 401, the method 400 comprises determining one or more segmentation parameters 211 based on analysis of a segmented reference Region of Interest (RoI) in a reference image 103. In an embodiment, determining the one or more segmentation parameters 211 may comprise, without limiting to, determining the one or more morphological characteristics of the segmented reference RoI 303, a position of the segmented reference RoI 303 within the reference image 103, an intensity distribution of the segmented reference RoI 303, and a background intensity distribution of a background of the segmented reference RoI 303.

In an embodiment, the background intensity distribution of the background may be determined using the following methods:

1. By determining a plurality of intensity distributions of a plurality of background pixels/points corresponding to the quadrants, with respect to centre of the segmented reference RoI 303. In an embodiment, the plurality of intensity distributions may be determined based on an amount of overlapping between the pixel intensities of the respective background of the plurality of background quadrants and pixel intensities of the segmented reference RoI 303.
2. By grouping pixels of the background into a plurality of background quadrants with the centre of the segmented reference RoI 303 as origin. Further, a background threshold corresponding to each of the plurality of background quadrants is determined based on the amount of overlapping between the pixel intensities of the respective background quadrant to the pixel intensities of the segmented reference RoI 303. Finally, the background intensity distribution corresponding to each of the plurality of background quadrants may be determined based on the corresponding background threshold.

In an embodiment, the intensity distribution of the segmented reference RoI 303 may be determined by generating a histogram of pixels in the segmented reference RoI 303 and determining one or more intensity ranges of the segmented reference RoI 303 based on the histogram and a predetermined threshold. In an embodiment, the one or more intensity ranges may be representative of the intensity distribution of the segmented reference RoI 303.

At block 403, the method 400 comprises determining a plurality of reference points 213 corresponding to the segmented reference RoI 303 based on one or more morphological characteristics of the segmented reference RoI 303. In an embodiment, determining the one or more morphological characteristics of the segmented reference RoI 303 may comprise, without limiting to, determining a short axis 303B and a longest diameter 303A of the segmented reference RoI 303. Further, determining the one or more morphological characteristics may include determining a size and a shape of the segmented reference RoI 303 based on length and coordinates of the short axis 303B and the longest diameter 303A of the segmented reference RoI 303.

At block 405, the method 400 comprises generating a plurality of translated points 215 on a current image 107, in which a target RoI 109 has to be segmented, by translating each of the plurality of reference points 213 onto the current image 107. In an embodiment, the reference image 103 and the current image 107 may be images of a single entity captured at different time periods.

At block 407, the method 400 comprises automatically selecting relevant seeds 311 in the current image 107, from the plurality of translated points 215, based on the one or more segmentation parameters 211. In an embodiment, the relevant seeds 311 in the current image 107 may be automatically selected by selecting one or more translated points 215 from the plurality of translated points 215 if an intensity of the one or more translated points 215 falls within the intensity distribution of the segmented reference RoI 303. Further, the relevant seeds 311 in the current image may be automatically selected based on the following criteria:
 1. When an intensity of the one or more translated points 215 does not fall within the background intensity distribution of the segmented reference RoI 303.
 2. When intensities of at least a predetermined number of neighbouring pixels of the one or more translated points 215 falls within the intensity distribution of the segmented reference RoI 303.
 3. When intensities of at least a predetermined number of neighbouring pixels of the one or more translated points 215 does not fall within a background intensity distribution range of the background.
 4. When an intensity of the one or more translated points 215 is less than an intensity distribution range of the segmented reference RoI 303 and the background intensity distribution range of the background.
 5. When an intensity of the one or more translated points 215 is greater than a highest intensity value of the intensity distribution of the segmented reference RoI 303 and a highest intensity value of the background intensity distribution range of the background.

At block 409, the method 400 comprises performing a multi-seed segmentation of the selected relevant seeds 311 for estimating and segmenting the Target RoI 109 in the current image 107. In an embodiment, the target RoI 109 is the propagated segmentation of the segmented RoI in the reference image 103. In an embodiment, a prerequisite condition for performing the segmentation of the target RoI 109 may be that the pixel intensities of the current image 107 must be quantitatively comparable or normalized to pixel intensities of the reference image 103.

Computer System

Figure 5:
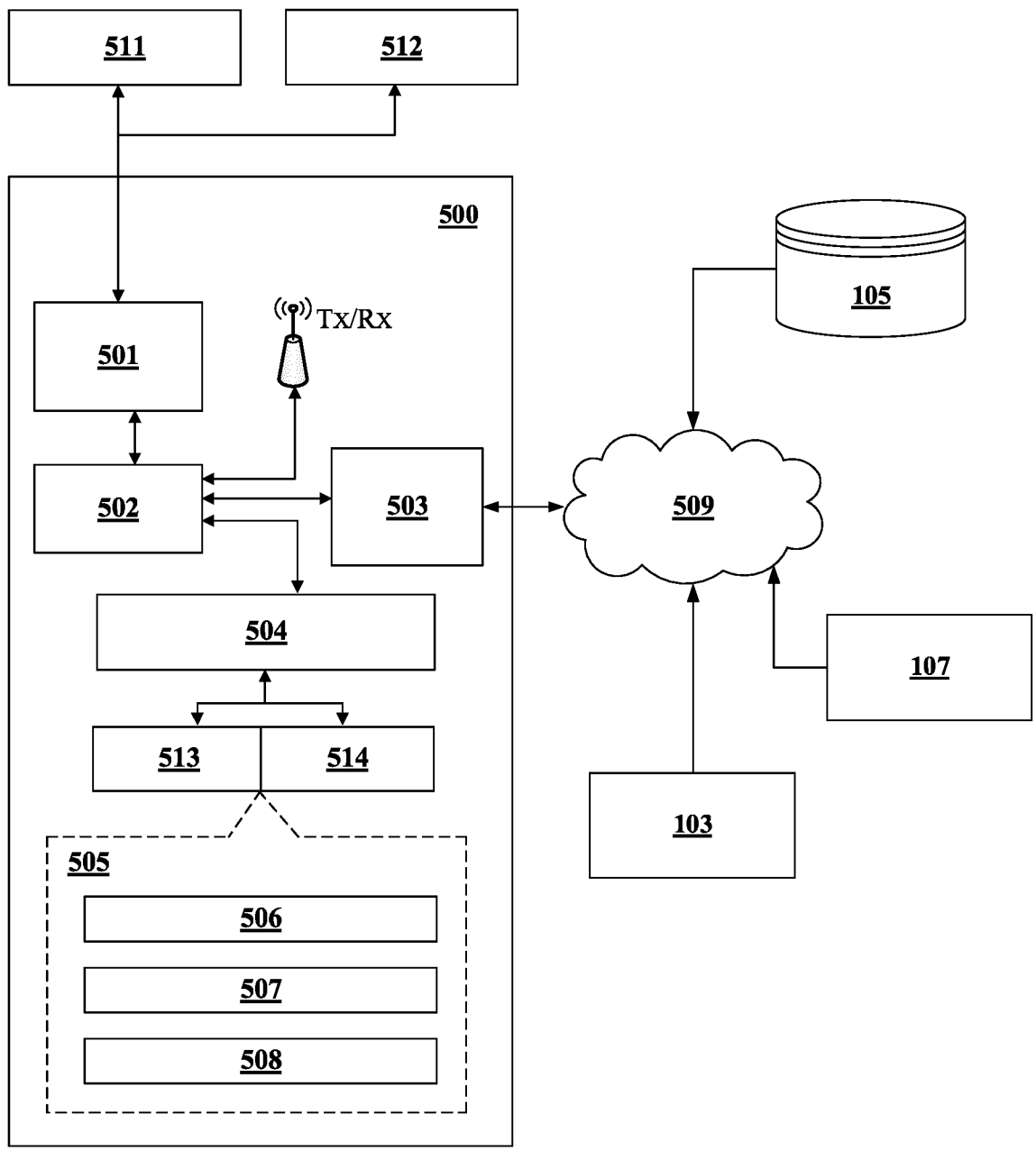
FIG. 5 illustrates a block diagram of an exemplary computer system for implementing embodiments consistent with the present disclosure.

FIG. 5 illustrates a block diagram of an exemplary computer system 500 for implementing embodiments consistent with the present disclosure. In an embodiment, the computer system 500 may be an image segmentation system 101, which is used for automatically propagating segmentation in medical images. The computer system 500 may include a central processing unit ("CPU" or "processor") 502. The processor 502 may comprise at least one data processor for executing program components for executing user- or system-generated business processes.

A user may include a person, a patient, a medical practitioner and/or a technologist, a person using the image segmentation system 101 and the like. The processor 502 may include specialized processing units such as integrated system (bus) controllers, memory management control units, floating point units, graphics processing units, digital signal processing units, etc.

The processor 502 may be disposed in communication with one or more input/output (I/O) devices (511 and 512) via I/O interface 501. The I/O interface 501 may employ communication protocols/methods such as, without limitation, audio, analog, digital, stereo, IEEE-1394, serial bus, Universal Serial Bus (USB), infrared, PS/2, BNC, coaxial, component, composite, Digital Visual Interface (DVI), high-definition multimedia interface (HDMI), Radio Frequency (RF) antennas, S-Video, Video Graphics Array (VGA), IEEE 802.n/b/g/n/x, Bluetooth, cellular (e.g., Code-Division Multiple Access (CDMA), High-Speed Packet Access (HSPA+), Global System For Mobile Communications (GSM), Long-Term Evolution (LTE) or the like), etc. Using the I/O interface 501, the computer system 500 may communicate with one or more I/O devices 511 and 512.

In some embodiments, the processor 502 may be disposed in communication with a communication network 509 via a network interface 503. The network interface 503 may communicate with the communication network 509. The network interface 503 may employ connection protocols including, without limitation, direct connect, Ethernet (e.g., twisted pair 10/100/1000 Base T), Transmission Control Protocol/Internet Protocol (TCP/IP), token ring, IEEE 802.11a/b/g/n/x, etc. Using the network interface 503 and the communication network 509, the computer system 500 may communicate with a reference database 105 for receiving a segmented reference Region of Interest (RoI) of a reference image 103. Further, the communication network 509 may be used to receive the reference image 103 and a current image 107 from one or more sources such as an X-Ray scanner.

The communication network 509 can be implemented as one of the several types of networks, such as intranet or Local Area Network (LAN) and such within the organization. The communication network 509 may either be a dedicated network or a shared network, which represents an association of several types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the communication network 509 may include a variety of network devices, including routers, bridges, servers, computing devices, storage devices, etc.

In some embodiments, the processor 502 may be disposed in communication with a memory 505 (for example, RAM 513 and ROM 514 as shown in FIG. 5) via a storage interface 504. The storage interface 504 may connect to memory 505 including, without limitation, memory drives, removable disc drives, etc., employing connection protocols such as Serial Advanced Technology Attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 505 may store a collection of program or database components, including, without limitation, user/application 506, an operating system 507, a web browser 508, and the like. In some embodiments, computer system 500 may store user/application data 506, such as the data, variables, records, and the like as described in this disclosure. Such databases may be implemented as fault-tolerant, relational, scalable, secure databases such as Oracle or Sybase.

The operating system 507 may facilitate resource management and operation of the computer system 500. Examples of operating systems include, without limitation, Apple Macintosh OS X, UNIX, Unix-like system distributions (e.g., Berkeley Software Distribution (BSD), Free-BSD, Net BSD, Open BSD, etc.), Linux distributions (e.g., Red Hat, Ubuntu, K-Ubuntu, etc.), International Business Machines (IBM) OS/2, Microsoft Windows (XP, Vista/7/8, etc.), Apple iOS, Google Android, Blackberry Operating System (OS), or the like.

A user interface may facilitate display, execution, interaction, manipulation, or operation of program components through textual or graphical facilities. For example, user interfaces may provide computer interaction interface elements on a display system operatively connected to the computer system 500, such as cursors, icons, check boxes, menus, windows, widgets, etc. Graphical User Interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, JavaScript, AJAX, HTML, Adobe Flash, etc.), or the like.

Furthermore, one or more computer-readable storage media may be utilized in implementing embodiments consistent with the present invention. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., non-transitory. Examples include Random Access Memory (RAM), Read-Only Memory (ROM), volatile memory, nonvolatile memory, hard drives, Compact Disc (CD) ROMs, Digital Video Disc (DVDs), flash drives, disks, and any other known physical storage media.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise. The enumerated listing of items does not imply that any or all the items are mutually exclusive, unless expressly specified otherwise.

The terms "a", "an" and "the" mean "one or more", unless expressly specified otherwise. A description of an embodiment with several components in communication with each other does not imply that all such components are required. On the contrary, a variety of optional components are described to illustrate the wide variety of possible embodiments of the invention.

When a single device or article is described herein, it will be clear that more than one device/article (whether they cooperate) may be used in place of a single device/article. Similarly, where more than one device or article is described herein (whether they cooperate), it will be clear that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERRAL NUMERALS

| Reference Number | Description |
| --- | --- |
| 100 | Environment |
| 101 | Image segmentation system |
| 103 | Reference image |
| 105 | Reference database |
| 107 | Current image |
| 109 | Target Region of Interest (RoI) |
| 201 | I/O interface |
| 203 | Processor |
| 205 | Memory |
| 207 | Data |
| 209 | Modules |
| 211 | Segmentation parameters |
| 213 | Reference points |
| 215 | Translated points |
| 219 | Other data |
| 221 | Parameter determination module |
| 223 | Reference point determination module |
| 225 | Seed generation module |
| 227 | Seed selection module |
| 229 | Segmentation module |
| 231 | Other modules |
| 301 | Exemplary reference image |
| 303 | Segmented reference RoI |
| 303A | Longest diameter |
| 303B | Short axis |
| 311 | Relevant seeds |
| 313 | Overlapping region |
| 501 | I/O Interface of the exemplary computer system |
| 502 | Processor of the exemplary computer system |
| 503 | Network interface |
| 504 | Storage interface |
| 505 | Memory of the exemplary computer system |
| 506 | User/Application |
| 507 | Operating system |
| 508 | Web browser |
| 509 | Communication network |
| 511 | Input devices |
| 512 | Output devices |
| 513 | RAM |
| 514 | ROM |

The invention claimed is:

1. A method of automatically propagating segmentation in a medical image, the method comprising:
   determining one or more segmentation parameters based on analysis of a segmented reference Region of Interest (RoI) in a reference image;
   determining a plurality of reference points corresponding to the segmented reference RoI based on one or more morphological characteristics of the segmented reference RoI;
   generating a plurality of translated points on a current image, in which a target RoI has to be segmented, by translating each of the plurality of reference points onto the current image;
   automatically selecting relevant seeds in the current image, from the plurality of translated points, based on the one or more segmentation parameters; and
   performing a multi-seed segmentation of the selected relevant seeds for estimating and segmenting the target RoI in the current image, wherein the target RoI is the propagated segmentation of the segmented RoI in the reference image and wherein pixel intensities of the current image are quantitatively comparable or can be normalized to pixel intensities of the reference image.

2. The method as claimed in claim 1, wherein the reference image and the current image are images of a single entity captured at different time periods.

3. The method as claimed in claim 1, wherein determining the one or more segmentation parameters comprises determining the one or more morphological characteristics of the segmented reference RoI, a position of the segmented reference RoI within the reference image, an intensity distribution of the segmented reference RoI, and a background intensity distribution of a background of the segmented reference RoI.

4. The method as claimed in claim 3, wherein determining the one or more morphological characteristics of the segmented reference RoI comprises:
   determining a short axis and a longest diameter of the segmented reference RoI; and
   determining a size and a shape of the segmented reference RoI based on length and coordinates of the short axis and the longest diameter of the segmented reference RoI.

5. The method of claim 3, wherein determining the background intensity distribution of the background comprises determining a plurality of intensity distributions of a plurality of background pixels/points corresponding to the quadrants, with respect to centre of the segmented reference RoI, based on an amount of overlapping between the pixel intensities of the respective background of the plurality of background quadrants and pixel intensities of the segmented reference RoI.

6. The method as claimed in claim 5, wherein determining the background intensity distribution of the background comprises:
   grouping pixels of the background into a plurality of background quadrants with the centre of the segmented reference RoI as origin;
   determining a background threshold corresponding to each of the plurality of background quadrants based on the amount of overlapping between the pixel intensities of the respective background quadrant to the pixel intensities of the segmented reference RoI; and
   determining the background intensity distribution corresponding to each of the plurality of background quadrants based on the corresponding background threshold.

7. The method as claimed in claim 3, wherein determining the intensity distribution of the segmented reference RoI comprises:
   generating a histogram of pixels in the segmented reference RoI; and
   determining one or more intensity ranges of the segmented reference RoI based on the histogram and a predetermined threshold, wherein the one or more intensity ranges is representative of the intensity distribution of the segmented reference RoI.

8. The method as claimed in claim 1, wherein automatically selecting the relevant seeds in the current image comprises selecting one or more translated points from the plurality of translated points if an intensity of the one or more translated points falls within the intensity distribution of the segmented reference RoI.

9. The method as claimed in claim 8, wherein automatically selecting the relevant seeds in the current image comprises selecting the one or more translated points if an intensity of the one or more translated points does not fall within the background intensity distribution of the segmented reference RoI.

10. The method as claimed in claim 9, wherein automatically selecting the relevant seeds in the current image comprises selecting the one or more translated points if intensities of at least a predetermined number of neighbouring pixels of the one or more translated points falls within the intensity distribution of the segmented reference RoI.

11. The method as claimed in claim 10, wherein automatically selecting the relevant seeds in the current image comprises selecting the one or more translated points if intensities of at least a predetermined number of neighbouring pixels of the one or more translated points does not fall within a background intensity distribution range of the background.

12. The method as claimed in claim 8, wherein automatically selecting the relevant seeds in the current image comprises determining if an intensity of the one or more translated points is less than an intensity distribution range of the segmented reference RoI and the background intensity distribution range of the background.

13. The method as claimed in claim 8, wherein automatically selecting the relevant seeds in the current image comprises determining if an intensity of the one or more translated points is greater than a highest intensity value of the intensity distribution of the segmented reference RoI and a highest intensity value of the background intensity distribution range of the background.

14. An image segmentation system for automatically propagating segmentation in a medical image, the image segmentation system comprising:
   a processor; and
   a memory, communicatively coupled to the processor, wherein the memory stores processor-executable instructions, which on execution, cause the processor to:
      determine one or more segmentation parameters based on analysis of a segmented reference Region of Interest (RoI) in a reference image;
      determine a plurality of reference points corresponding to the segmented reference RoI based on one or more morphological characteristics of the segmented reference RoI;

generate a plurality of translated points on a current image, in which a target RoI has to be segmented, by translating each of the plurality of reference points onto the current image;

automatically select relevant seeds in the current image, from the plurality of translated points, based on the one or more segmentation parameters; and perform a multi-seed segmentation of the selected relevant seeds to estimate and segment the target RoI in the current image, wherein the target RoI is the propagated segmentation of the segmented RoI in the reference image and wherein pixel intensities of the current image are quantitatively comparable or can be normalized to pixel intensities of the reference image.

15. The image segmentation system as claimed in claim 14, wherein the reference image and the current image are images of a single entity captured at different time periods.

16. The method according to claim 2, wherein reference image and the current image are images of a same human being.

17. The method according to claim 16, wherein the reference image is an image of the human being captured during an initial medical image study of the human being and the current image is an image of a same human being captured during a subsequent medical image study of the same human being.

18. The image segmentation system according to claim 15, wherein reference image and the current image are images of a same human being.

19. The image segmentation system according to claim 18, wherein the reference image is an image of the human being captured during an initial medical image study of the human being and the current image is an image of a same human being captured during a subsequent medical image study of the same human being.

* * * * *